United States Patent [19]
Kojima et al.

[11] 4,086,138
[45] Apr. 25, 1978

[54] PROCESS FOR PRODUCING GLUCOSE ISOMERASE

[75] Inventors: Ichiro Kojima; Hiroshi Sato, both of Yokohama; Yasuo Fujiwara, Tokyo, all of Japan

[73] Assignee: Nippon Oil Company, Ltd., Japan

[21] Appl. No.: 763,540

[22] Filed: Jan. 28, 1977

[30] Foreign Application Priority Data

Feb. 3, 1976 Japan .................................. 51-9962

[51] Int. Cl.$^2$ ..................... C12D 13/10; C12D 13/02; C07G 7/02
[52] U.S. Cl. .................................... 195/65; 195/31 F; 195/62; 195/66 R
[58] Field of Search ................ 195/62, 66 R, 65, 31 F

[56] References Cited

U.S. PATENT DOCUMENTS

| | | | |
|---|---|---|---|
| 3,826,714 | 7/1974 | Suekane et al. | 195/31 F |
| 3,956,066 | 5/1976 | Coker et al. | 195/31 F |

OTHER PUBLICATIONS

Tunail, et al., "A New Coryneform Hydrogen Bacterium Corynebacterium Autotrophicam Strain 7 C.I. Characterization of the Wild Type Strain", *Chemical Abstracts,* vol. 82, No. 21, p. 246, (1975), Abs. No. 135342b.

*Primary Examiner*—Raymond N. Jones
*Assistant Examiner*—Thomas G. Wiseman
*Attorney, Agent, or Firm*—Wenderoth, Lind & Ponack

[57] ABSTRACT

A process for producing glucose isomerase which comprises cultivating a glucose isomerase-producing bacterium belonging to the genus Corynebacterium under aerobic conditions in a culture medium containing carbon sources and nitrogen sources and separating the glucose isomerase-containing cells from the culture broth, and a process for producing fructose which comprises contacting glucose in an aqueous medium with the glucose isomerase-containing cells of a bacterium belonging to the genus Corynebacterium or glucose isomerase separated therefrom.

8 Claims, No Drawings

PROCESS FOR PRODUCING GLUCOSE ISOMERASE

This invention relates to a process for producing glucose isomerase useful for isomerizing glucose to fructose. More specifically, it relates to a process for producing glucose isomerase, which comprises cultivating a glucose isomerase-producing microorganism belonging to the genus Corynebacterium heretofore not known to include a glucose isomerase-producing species, and separating the glucose isomerase-containing cells from the culture broth.

The invention also relates to a process for producing fructose which comprises contacting glucose in an aqueous medium with the glucose isomerase-containing cells obtained by the above process or glucose isomerase separated therefrom.

The demand for fructose has increased in recent years because of its increased acceptance as a raw material for liquid sugars, low-caloric sweetenings, and therapeutic and prophylactic sweetenings or diabetes and hepatic diseases. With the increased demand for fructose, a process for producing fructose from glucose using glucose isomerase has come into practical operation. Microorganisms reportedly having the ability to produce glucose isomerase include bacteria belonging to the genus Bacillus, Escherichia, Aerobacter, Lactobacillus, Arthrobacter, Pseudomonas, and Brevibacterium; and ray fungi belonging to the genus Streptomyces, Nocardia, Micromonospora, Microbispora, and Streptosporangium.

It has been quite unknown that a microorganism belonging to the genus Corynebacterium produces glucose isomerase. The present inventors screened microorganisms capable of producing glucose isomerase in feasible quantities, and discovered glucose isomerase-producing microorganisms which are strains isolated from the soil and belonging to the genus Corynebacterium. It has been found on further investigation that these glucose isomerase-producing strains of the genus Corynebacterium can produce glucose isomerase in amounts comparable to conventional glucose isomerase-producing microorganisms, and glucose can be easily isomerized to fructose by contacting it with the glucose isomerase-containing cells or glucose isomerase separated therefrom.

It is an object of this invention therefore to provide a process for producing glucose isomerase.

Another object of this invention is to disclose the existence of microorganisms of the genus Corynebacterium which have the ability to produce glucose isomerase, thus contributing further to the art to which the present invention pertains.

Still another object of this invention is to provide a process for producing fructose from glucose using the glucose isomerase obtained by the above process.

The above and other objects and advantages of the invention will become more apparent from the following description.

The micoorganisms of the genus Corynebacterium isolated from the soil by the present inventors have the microbiological properties to be described, and have been identified as novel species of the genus Corynebacterium. Typical strains of these novel species were named Corynebacterium candidus (FERM-P No. 3285), and Corynebacterium cerenus (FERM-P No. 3286), and deposited in Fermentation Research Institute, Agency of Industrial Science and Technology, Japan. These strains were also deposited in American Type Culture Collection as Corynebacterium condidus ATCC 31261 and Corynebacterium cerenus ATCC 31262.

The microbiological properties of these strains are as follows:

Corynebacterium candidus (FERM-P No. 3285; ATCC 31261)

1. Morphological properties
    Morphology: rods with a size of 0.8–1.0 × 4–5 microns which are curved; some of them connected in a V-form.
    Motility: None
    Gram staining: Positive
    Spores: none
2. Properties in cultivation
    Nutrient agar plate culture: growth medium, peripheral edge irregular, flat, opaque, shining, milky white.
    Nutrient agar slant culture: growth medium, filiform, opaque, shining, milky white.
    Nutrient broth: forming fragile rings, clear, sedimentation.
    Growth temperature: 25° to 37° C
    Optimal pH: 4.5 to 9
    Oxygen demand: aerobic
3. Physiological properties
    Litmus milk: slightly decolorized, and very slowly peptonized
    Gelatin: not liquefied
    Hydrogen sulfide: generated
    Indole: not generated
    Starch: decomposed
    Nitrate: reduced
    Catalase: produced
    Sugar metabolism determined by the Hugh and Leifson method: neither acids nor gases are generated from arabinose, xylose, fructose, galactose, glucose, mannose, mannitol, sorbitol, lactos, maltose, sucrose, raffinose, and glycerin
    Asparagine: decomposed
    Citric acid: assimilated
    Acid fastness: none Corynebacterium cerenus (FERM-P No. 3286; ATCC 31262)

This strain differs from the Corynebacterium candidus in the following respects.
    Properties in a bouillon-agar plate culture: growth medium, peripheral edge wavy, raised, opaque, shining, milky white.
    Physiological properties in sugar metabolism by the Hugh and Leifson method:
        An acid is generated from mannitol.

The above microbiological properties were compared with the description of "Bergey's Manual of Determinative Bacteriology", 7th edition, but no applicable strain was found. As a result, the above strains were identified as novel strains of the genus Corynebacterium, and named as described hereinabove.

The enzyme activity is measured by the following method in the present invention.

Glucose is dissolved in a 1/15 M phosphate buffer (pH 7.0) to a glucose concentration of 400 mg/ml, and cobalt chloride is dissolved in it to a cobalt chloride concentration of 0.5 mM. Cells separated by centrifugal separation from the culture broth are added to 2.0 ml of the resulting solution and reacted at 70° C for 1 hour. Then, 2.0 ml of 5% perchloric acid is added to the reaction mixture to terminate the reaction. The reaction mixture is centrifuged, and fructose in the resulting supernatant liquid is determined by a carbazole-cysteine-sulfuric acid reaction method. The enzyme activity which affords fructose in an amount of 1 mg for 1 hour is defined as 1 unit (U).

According to this invention, the glucose isomerase-producing strain of the genus Corynebacterium is cultivated under aerobic conditions in a culture medium containing a carbon source and a nitrogen source, and the glucose isomerase-containing cells are recovered from the resulting culture broth.

The culture medium may contain inorganic salts and an antifoamer in addition to the carbon and nitrogen sources. Examples of the carbon source are sugars, carbohydrates, alcohols, and hydrocarbons. In the present invention, especially good results can be obtained by adding xylose as a substance inducing the production of glucose isomerase. Xylose alone may be used as a carbon source. Examples of the nitrogen source are corn steep liquor, yeast extract, meat extract, peptone, chopped fish powder, ammonium salts, nitrate salts, and urea.

The amounts of the carbon and nitrogen sources can be varied as needed. For example, the amount of the carbon source is about 5 g/liter to about 50 g/liter, and the amount of the nitrogen source is about 2 g/liter to about 20 g/liter.

Examples of the inorganic salts are phosphate salts, magnesium salts, iron salts, zinc salts, cobalt salts, calcium salts, manganese salts, molybdenum salts, and copper salts. The amount of the inorganic salt may be small. For example, the preferred amount is about 0.3 to 1 mg/liter in the case of an iron salt as $FeSO_4.7H_2O$; and about 5 to 20 mg/liter in the case of a cobalt salt as $CoCl_2.6H_2O$.

The composition of the culture medium can be changed as needed, and the ingredients can be supplementally added during the culticaction.

Cultivation is performed under aerobic conditions, and shaking culture and aeration-stirring culture, for example, are used preferably. The culticaction temperature is about 20° to about 40° C, and the pH of the culture medium is about 3.5 to about 9.5, preferably about 4 to about 6. The cultivation can be performed usually for 1 to 5 days.

According to the process of this invention cultivation of a glucose isomerase-producing strain of the genus Corynebacterium in the above manner commercially advantageously results in the accumulation of glucose isomerase in the cells of the microorganism. The glucose isomerase-containing cells can be separated from the culture broth by, for example, centrifugal separation.

It has been found that glucose can be enzymatically isomerized to fructose by utilizing glucose isomerase in any desired form such as cells, as obtained by the aforementioned cultivation process, their pulverized product, dried product, or extract, a crude enzyme, or a purified enzyme. Thus, according to another aspect of the invention, there is provided a process for producing fructose which comprises contacting glucose in an aqueous medium with glucose isomerase-containing cells of a strain of the genus Corynebacterium or glucose isomerase separated therefrom.

The extraction and separation of the enzyme from the glucose isomerase-containing cells and its purification can be performed by methods known to be used in the extraction and separation of glucose isomerase from the glucose isomerase-containing cells obtained by utilizing known glucose isomerase-producing microorganisms. For example, the glucose isomerase-containing cells can be crushed by milling, application of ultrasonic waves, or abrupt changing of pressure to separate the glucose isomerase from the cells. Or self-digestion of the cells may be utilized in this separating procedure. Furthermore, the crude enzyme taken out of the cells can be purified by a suitable combination of known means such as salting out with ammonium sulfate, precipitation with organic solvents, gel filtration, or column chromatography.

According to one embodiment of separating the enzyme from the cells in the culture broth and purifying it, the cells obtained by centrifugal separation from the culture broth is first crushed by application of ultrasonic waves in an aqueous medium. Acetone is added to the supernatant liquid obtained by centrifugal separation from the liquid containing the crushed cells, and precipitated fractions are collected. The fractions are subjected to liquid chromatography using a column packed with DEAE cellulose or DEAE-SEPHADEX (a product of Farmacia Company) to purify the enzyme.

The contacting of the glucose isomerase in any desired form obtained by the process of this invention with glucose is performed by any means which can maintain both in contact with each other at the isomerization temperature and pH. The preferred isomerization temperature is about 50° to about 80° C. More preferably, the temperature is about 60° to about 75° C. The pH at the time of isomerization is preferably about 6 to about 10, more preferably about $7 \pm 0.5$. The isomerization time can be varied according to other conditions, and is usually 1 to 8 hours, preferably about 5 to 30 hours. The reaction is carried out until glucose reaches an equilibrium with fructose formed. Preferably, the reaction is carried out in an aqueous medium. The reaction can be performed in the further presence of a promotor substance capable of forming an ion having an action of promoting isomerization, such as an Mg ion or Co ion.

Separation of fructose from the isomerization reaction mixture and its purification can be performed by known means such as crystallizing fractionation by the formation of a double salt, or adsorption to an ion exchange resin.

The following Examples illustrate the processes of this invention in greater detail.

EXAMPLE 1

Corynebacterium candidus (FERM-P No. 3285) was inoculated in a 500 ml conical flask containing 100 ml of a sterilized culture medium containing deionized pure water, and per liter of the water, 10 g of xylose, 10 g of peptone, 0.4 g of $KH_2PO_4$, 1.5 g of $Na_2HPO_4.12H_2O$ and 0.5 g of $MgSO_4.7H_2O$ at varying initial pH values. It was cultivated with shaking at 30° C for 2 days. The concentrations of glucose isomerase produced in the culture broth according to the pH values are shown in Table 1.

The concentration of glucose isomerase produced in the culture broth was measured by the following method. 10 ml of the culture broth was centrifuged for 5 minutes at 10,000 G. The precipitated cells were charged into a test tube with an outside diameter of 15 mm containing 2.0 ml of a glucose isomerase reaction solution containing a 1/15 M phosphoric acid buffer (pH 7.0) and per liter of the phosphoric acid buffer, 400 g of glucose and 0.5 millimole of $CoCl_2.6H_2O$, and reacted at 70° C for 1 hour. Then, 2.0 ml of 5% perchloric acid was added to terminate the reaction. Fructose formed in the reaction mixture was determined by the carbazole-cysteine-sulfuric acid reaction method, and the concentration of glucose isomerase was calculated.

Table 1

| Initial pH | Concentration of glucose isomerase produced (U/ml) |
| --- | --- |
| 4.0 | 9.6 |
| 4.5 | 11.2 |
| 5.0 | 10.4 |
| 6.0 | 10.4 |
| 7.0 | 5.9 |

EXAMPLE 2

Using a culture medium having an initial pH of 4.5 as used in Example 1 as a basic medium, $FeSO_4.7H_2O$ and $CoCl_2.6H_2O$ were added in various amounts per liter of the water, and the culture medium was sterilized. Then, 100 ml. of the resulting culture medium was placed in a 500 ml. conical flask, and Corynebacterium candidus was inoculated in the culture medium in the same way as in Example 1. It was cultivated with shaking at 30° C for 2 days. The concentrations of the glucose isomerase produced in the culture broth were measured, and the results are shown in Table 2.

Table 2

| Effects of adding Fe salt and Co salt | | |
| --- | --- | --- |
| Amount (mg) | | Concentration of glucose isomerase |
| $FeSO_4.7H_2O$ | $CoCl_2.6H_2O$ | produced (U/ml) |
| 0 | 10 | 17.5 |
| 0.3 | 10 | 21.0 |
| 0.5 | 10 | 23.0 |
| 1.0 | 10 | 20.5 |
| 2.0 | 10 | 19.3 |
| 10.0 | 10 | 19.3 |
| 0.5 | 0 | 15.5 |
| 0.5 | 2 | 19.0 |
| 0.5 | 5 | 21.0 |
| 0.5 | 20 | 22.5 |

EXAMPLE 3

Using a culture medium obtained by adding 0.5 mg of $FeSO_4.7H_2O$ and 10 mg of $CoCl_2.6H_2O$ to the basic culture medium used in Example 2, the same procedure as in Example 2 was repeated except that Corynebacterium cerenus (FERM-P No. 3286) was used instead of the Corynebacterium candidus. The concentration of glucose isomerase produced in the culture broth was 19.1 U per ml of the culture broth.

What we claim is:

1. A process for producing glucose isomerase which comprises cultivating Corynebacterium candidus under aerobic conditions in a culture medium containing carbon sources and nitrogen sources and separating the glucose isomerase-containing cells from the culture broth.

2. The process of claim 1 wherein the *Corynebacterium candidus* is the strain *Corynebacterium candidus* FERM-P3285.

3. The process of claim 1 wherein the cultivation is carried out at a temperature of about 20° to about 40° C.

4. The process of claim 1 wherein the cultivation is carried out at a pH of about 3.5 to about 9.5.

5. A process for producing glucose isomerase which comprises cultivating *Corynebacterium cerenus* under aerobic conditions in a culture medium containing carbon sources and nitrogen sources and separating the glucose isomerase-containing cells from the culture broth.

6. The process of claim 5 wherein the *Corynebacterium cerenus* is the strain *Corynebacterium cerenus* FERM-P3286.

7. The process of claim 5 wherein the cultivation is carried out at a temperature of about 20° to about 40° C.

8. The process of claim 5 wherein the cultivation is carried out at a pH of about 3.5 to about 9.5.

* * * * *